United States Patent [19]

Miller et al.

[11] 4,369,181

[45] Jan. 18, 1983

[54] PROCESS FOR TREATING PROLIFERATIVE SKIN DISEASES USING CERTAIN 6,8-SUBSTITUTED RIBOFURANOSYLPURINE-3',5'-CYCLIC PHOSPHATES

[75] Inventors: Jon P. Miller, Foster City; Wesley W. Zmolek, Fremont, both of Calif.

[73] Assignee: SRI International, Menlo Park, Calif.

[21] Appl. No.: 290,223

[22] Filed: Aug. 5, 1981

[51] Int. Cl.³ .................. A61K 31/70; C07H 19/20
[52] U.S. Cl. .................................. 424/180; 536/27; 536/28
[58] Field of Search ............... 424/180; 536/26, 27, 536/28

[56] References Cited

U.S. PATENT DOCUMENTS

| | | | |
|---|---|---|---|
| 4,048,307 | 9/1977 | Yokota et al. | 536/27 |
| 4,058,659 | 11/1977 | Robins et al. | 536/27 |
| 4,208,406 | 6/1980 | Lapinet et al. | 536/24 |
| 4,211,770 | 7/1980 | Voorhees | 424/180 |
| 4,235,887 | 11/1980 | Voorhees et al. | 424/180 |

Primary Examiner—Johnnie R. Brown
Attorney, Agent, or Firm—Thomas E. Ciotti

[57] ABSTRACT

Proliferative skin diseases such as psoriasis are treated by topically administering cAMP analogs of the following formula to the afflicted skin site at a dose that preferentially and significantly activates type II protein kinase:

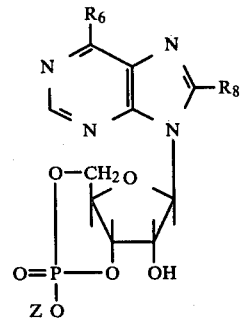

where:

$R_6$ is:
(i) —$NR_1 R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the —$NR_1 R_2$ group is 4 or 5, or
(ii) —XR where X is a chalcogen atom of atomic number 8 or 16 and R is alkyl of 4 or 5 carbon atoms, $R_8$ is:
(i) —X—$(CH_2)_n R_3$ where X is defined previously, n is an integer in the range of 1 to 3, inclusive, $R_3$ is hydrogen, alkyl of 1 to 7 carbon atoms, or phenyl substituted with 0 to 1, inclusive, nitro, halo of atomic number 9 to 35, inclusive, methoxy, hydroxy or methyl, or
(ii) —$NR_4 R_5$ wherein $R_4$ and $R_5$ are independently selected from the group consisting of hydrogen, alkyl of 1 to 8 carbon atoms, and phenalkyl of 7 to 9 carbon atoms with the provisos that only one of $R_4$ and $R_5$ may be hydrogen and the total number of carbon atoms in the —$NR_4 R_5$ group is in the range of 1 to 9, inclusive, and Z is hydrogen, an alkali metal cation or ammonium.

15 Claims, 1 Drawing Figure

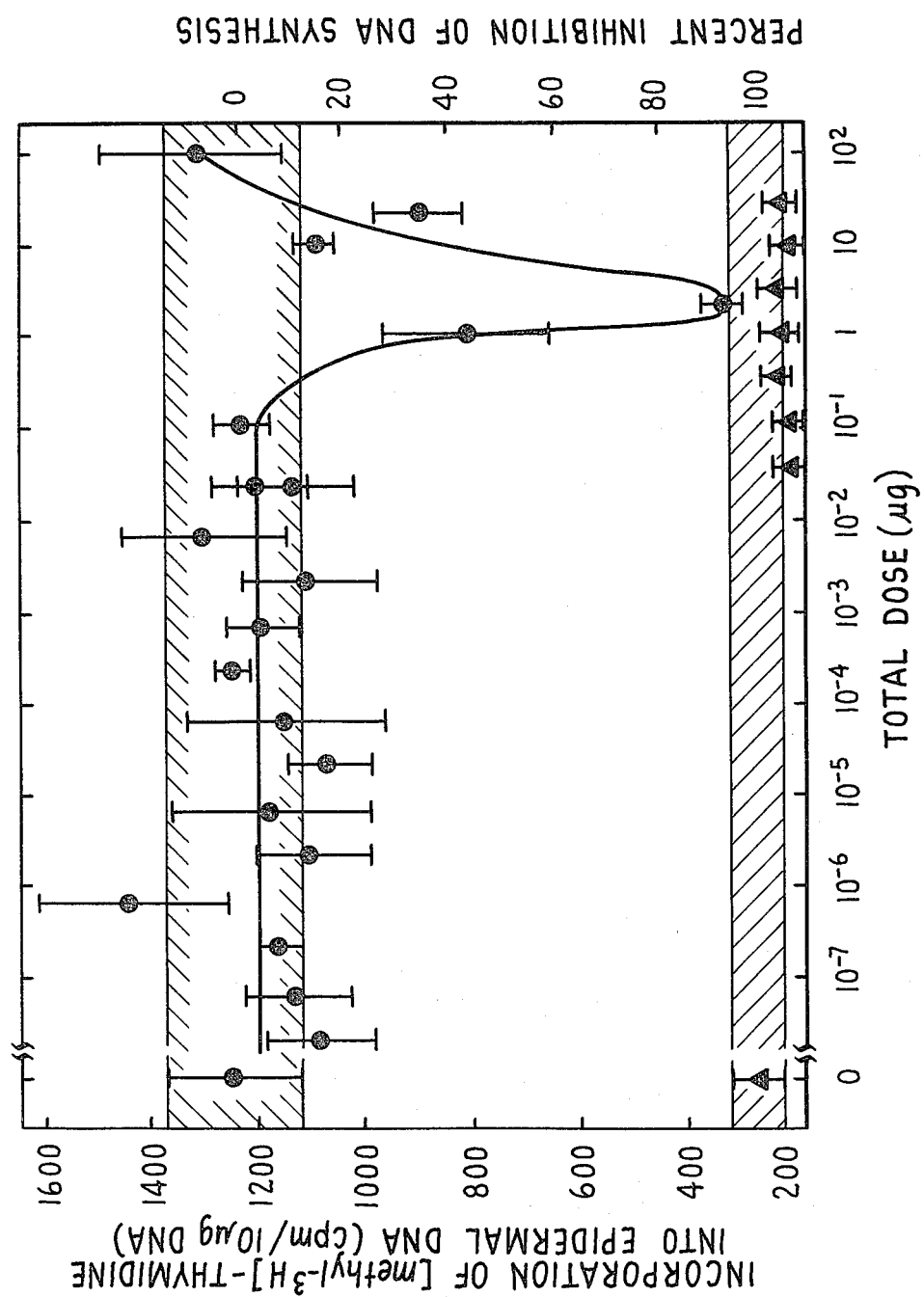

PROCESS FOR TREATING PROLIFERATIVE SKIN DISEASES USING CERTAIN 6,8-SUBSTITUTED RIBOFURANOSYLPURINE-3',5'-CYCLIC PHOSPHATES

REFERENCE TO GOVERNMENT GRANT

The invention described herein was made in the course of work under a grant or award from the Department of Health, Education and Welfare.

TECHNICAL FIELD

The invention relates to treating proliferative skin diseases with certain 6,8-substituted ribofuranosylpurine-3',5'-cyclic phosphates.

BACKGROUND ART

Psoriasis is perhaps the most prevalent proliferative skin disease. A recent review article, "Research Needs in 11 Major Areas in Dermatology", J Invest Derm 73:402–413, 1979, reports estimates that up to 4% of the U.S. population suffers from psoriasis. Psoriasis is believed to be a multifactorial genetic disease. Individuals that are genetically predisposed to psoriasis susceptibility develop the disease either spontaneously or in an area of damaged skin. The disease is characterized by uncontrolled benign growth of the epidermis and psoriatic epidermis exhibits (1) a marked increase in proliferation and (2) reduced terminal differentiation. Accordingly, much of the research on the etiology and treatment of psoriasis has focused on the factors that control epidermal growth and differentiation and on the pharmocological modulation of one or more of those factors.

A variety of therapies are currently used to treat psoriasis including dialysis, photochemotherapy, systemic chemotherapy, and topical chemotherapy. Topical chemotherapy is probably the most widely used. Tar, retinoids, anthralin, corticosteroids and antimetabolites are among the agents currently used to treat psoriasis. Cyclic adenosine monophosphate (cAMP) is among the factors that are believed to be critical regulators of cell physiology and, correlatively, derangement of the epidermal cAMP system is associated with psoriasis. Accordingly, cAMP and many derivatives thereof have been considered as antipsoriatic agents. In this regard U.S. Pat. Nos. 4,007,268 and 4,207,315 propose the use of certain 9-$\beta$-D-ribofuranosyladenine-3',5'-cyclic phosphates to treat proliferative skin diseases such as psoriasis. These compounds are analogs of the cyclic nucleotides that are used in the present invention. Comparative tests between some of these analogs and the nucleotides used in the present invention show the latter to have unexpected superior antipsoriatic activity of the analogs that were tested.

U.S. Pat. No. 4,058,659 describes a genus of 6,8-substituted-9-$\beta$-D-ribofuranosylpurine-3', 5'-cyclic phosphates that includes some, but not all, of the cyclic nucleotides that are used in the present invention. The compounds of the genus are analogs of the naturally occurring purine nucleotides and are said to be more resistant to phosphodiesterase attack than the natural compounds. The compounds are described as exhibiting, inter alia, phosphodiesterase inhibition, protein kinase activation, and adenyl cyclase inhibition activities. In this regard the first two activities—phosphodiesterase inhibition and protein kinase activation—are generally considered to be characteristic of compounds that are useful to treat psoriasis. However, applicant's findings show that topical antipsoriatic activity cannot, however, be inferred from such activities because all compounds that possess such activities are not practical antipsoriatic agents. The third activity—adenyl cyclase inhibition—is not characteristic of such compounds and indeed would be more characteristic of compounds that promote proliferative skin diseases.

As described in detail below, applicants' investigations also clearly indicate that the effectiveness of a given cAMP analog as a topical antipsoriatic agent cannot be predicted from the chemical structure of the analog.

DISCLOSURE OF THE INVENTION

Applicants' invention rests on their finding that a select group of cAMP analogs possess unexpected effectiveness as antipsoriatic agents when applied topically.

Accordingly, one aspect of the invention is a process for treating a proliferative skin disease comprising topically administering to the afflicted site on the skin of the patient a therapeutically effective amount of a compound of the formula

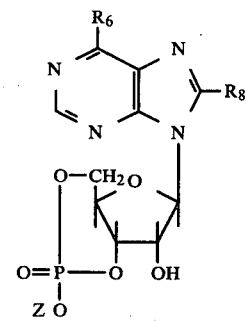

where:

$R_6$ is:

(i) $-NR_1 R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the $-NR_1 R_2$ group is 4 or 5, or (ii) $-XR$ where X is a chalcogen atom of atomic number 8 or 16 and R is alkyl of 4 or 5 carbon atoms, $R_8$ is:

(i) $-X-(CH_2)_n R_3$ where X is defined previously, n is an integer in the range of 1 to 3, inclusive, $R_3$ is hydrogen, alkyl of 1 to 7 carbon atoms, or phenyl substituted with 0 to 1, inclusive, nitro, halo of atomic number 9 to 35, inclusive, methoxy, hydroxy or methyl, or (ii) $-NR_4 R_5$ wherein $R_4$ and $R_5$ are independently selected from the group consisting of hydrogen and alkyl of 1 to 8 carbon atoms, and phenalkyl to 7 to 9 carbon atoms, with the provisos that only one of $R_4$ and $R_5$ may be hydrogen and the total number of carbon atoms in the $-NR_4 R_5$ group is in the range of 1 to 9, inclusive, and Z is hydrogen, an alkali metal cation or ammonium.

Another aspect of the invention is a topical dosage form for treating a proliferative skin disease comprising a therapeutically effective amount of at least one of the compounds of formula (1) admixed with a pharmaceutically acceptable topical carrier.

BRIEF DESCRIPTION OF THE DRAWING

The drawing is a graph depicting the antipsoriatic activity of one of the nucleotides of formula (1).

MODES FOR CARRYING OUT THE INVENTION

As used herein the term "proliferative skin diseases" means nonmalignant conditions of the skin that are characterized by epidermal cell proliferation or incomplete cell differentiation. These conditions may occur spontaneously or be induced by means external to the body such as exposure to radiation or chemicals. Such diseases include psoriasis, atopic dermatitis, nonspecific dermatitis, primary irritant contact dermatitis, allergic contact dermatitis, ichthyosis, epidermolytic hyperkeratosis, premalignant sun-induced keratosis, nonmalignant keratosis, and seborrheic dermatitis. It also includes ailments such as mange that are specific to non-human animals. The method may be used to treat humans and other animals such as domestic animals, pets, and sport animals.

Proliferative skin diseases are treated according to the invention by administering one or more of the cyclic nucleotides of formula (1) above topically to the afflicted site at a therapeutically effective dose. The nucleotide will usually be applied to the afflicted skin site in a conventional topical dosage form such as an ointment, cream, jelly, paste, lotion, shampoo or spray. Such dosage forms comprise the nucleotide formulated with one or more pharmaceutically acceptable topical vehicles such as petrolatum, polyethylene glycol, gelatin, isopropyl myristate, polyvinyl alcohol, and the like. The formulations may also include additives such as emmolients, stabilizers, surfactants, skin penetration altering agents and pigments. If controlled, continuous release of the nucleotide to the afflicted site is desired, such as if the nucleotide has a short half life in vivo, the nucleotide may be incorporated into known controlled release dosage forms that monitor the rate release of drug to the skin by diffusion, osmosis, dissolution, iontophoresis, or erosion. The nucleotides of formula (1) are generally stable at pHs in the range of about 3 to 9 and thus the formulation containing them should have pHs in this range. Preferably, the pH of the formulation is approximately neutral so as to be substantially nonirritating to the skin. When applied as a conventional dosage form in which the nucleotide is dissolved in the vehicle, the maximum concentration of the nucleotide in the formulation will, of course, depend on its solubility of the nucleotide in the vehicle. In this regard, the nucleotides are generally soluble in water and the use of water-based vehicles in the formulation will permit a wide range of nucleotide concentrations to be employed. Typically, the concentration of the nucleotide in conventional topical dosage forms will be in the range of 0.0001% to 1% by weight, more usually 0.001% to 0.1% by weight, of the dosage form.

The dosage regimen that is used in administering the nucleotides of formula (1) to the patient will depend upon the particular nucleotide. Animal model tests indicate that the antipsoriatic activity of at least some of the nucleotides occurs over a limited dose range. This is believed to be due to dose dependent preferential activation of either type I protein kinase or type II protein kinase. Preferential activation of type II protein kinase is associated with reduced epidermal proliferation whereas preferential activation of type I protein kinase may exacerbate the condition, if anything. Therefore, in functional terms, a therapeutic dose is one that preferentially and significantly activates type II protein kinase in the individual being treated. The therapeutic dose range for a given nucleotide may be determined empirically using the animal model described in the examples, infra. Therapeutic dose ranges for other animal species will approximate that of the model since the mode of administration is topical rather than systemic and, therefore, is substantially independent of individual body weight or serum volume. Animal model tests indicate the therapeutic dose range for the nucleotides will usually be between about 0.01 to 10 mcg/cm$^2$ of area treated, more usually about 0.1 to 1 mcg/cm$^2$ of area treated. Conventional dosage forms that do not release the nucleotide to the skin at a controlled rate over a prolonged time will normally be reapplied to the afflicted site on a twice daily basis in the above amounts. Controlled release dosage forms will be designed to administer the nucleotide at a rate that maintains the concentration of the nucleotide in the epidermis at a therapeutic level. Based upon the concentration of the nucleotide that would be expected to preferentially activate the type II protein kinase, that concentration is estimated to be in the range of about 0.0025 to 0.25 mcg/cm$^3$ of skin.

As indicated above, the substituent on the 6 position of the purine group of the nucleotide, designated $R_6$ in formula (1), may be a certain alkyl-substituted amino, an N-heterocyclic radical, an alkylthio, or an alkoxy group. The amino group may be mono- or di-alkyl substituted provided the total number of carbon atoms in the amino group is 4 or 5. Preferably the alkyl(s) is/are straight chain (except for cyclopentyl). Examples of such groups are n-butylamino, n-pentylamino, isobutylamino, isopentylamino, cyclopentylamino, methylpropylamino, methylisopropylamino, diethylamino, ethylpropylamino, and ethylisopropylamino. The N-heterocyclic radicals that $R_6$ may represent are saturated. Examples of such radicals are N-piperidyl and N-pyrrolidyl. The alkyl groups of the alkylthio or alkoxy radicals represented by $R_6$ may be branched or straight chain. Preferably the alkyl group of these radicals is straight chain. Examples of such radicals are n-butylthio, isobutylthio, n-pentylthio, isopentylthio, n-butoxy, isobutoxy, n-pentoxy, and isopentoxy. $R_6$ is preferably n-butylamino.

The substituent on the 8 position of the purine group of the nucleotide, designated $R_8$ in formula (1), represents certain alkylthio, phenylalkylthio, alkoxy, phenylalkoxy, mono-or diakylamino or phenalkylamino groups. The alkyl groups in these radicals are preferably straight chain. Examples of such groups are methylthio, ethylthio, n-hexylthio, 3-methylhexylthio, n-decylthio, methoxy, propoxy, n-heptoxy, n-nonoxy, benzylthio, p-chlorobenzylthio, m-fluorobenzylthio, p-nitrobenzylthio, o-chlorobenzylthio, p-methoxybenzylthio, p-methylbenzylthio, phenethylthio, phenpropylthio, benzoxy, phenpropoxy, methylamino, dimethylamino, ethylamino, diethylamino, n-propylamino, di-n-propylamino, hexylamino, octylamino, benzylamino, phenethylamino, and phenpropylamino. $R_8$ is preferably benzylthio.

As indicated in formula (1) the nucleotides may be in the form of a free base or an alkali metal or ammonium salt. As used herein, the term "ammonium salts" include primary, secondary and tertiary ammonium salts. A preferred salt is the sodium salt.

The cyclic nucleotides of formula (1) may be prepared by the reaction schemes disclosed in U.S. Pat. No. 4,058,659, which disclosure is incorporated herein by reference. The following examples further describe processes for synthesizing these nucleotides. Unless indicated otherwise percentages are given by weight in the Examples.

EXAMPLE 1

Preparation of 8-(benzylthio)-6-(n-butylamino)-9-($\beta$-D-ribofuranosyl)-purine cyclic 3', 5'-phosphate Method A. A solution of 2'-O-acetyl-8-(benzylthio)-6-chloro-9-($\beta$-D-ribofuranosyl)purine cyclic 3', 5'-phosphate sodium salt (3.5 g. 5.25 mmol) in 50 ml of $H_2O$ and 10 ml of n-butylamine was stirred overnight at room temperature. The solvent was evaporated and the residue triturated twice with ether, dissolved in $H_2O$, and acidified to pH 1 with 1 N HCl. The crude solid was filtered and dissolved in EtOH. Five volumes of ether was added to the EtOH and the precipitated solid collected: recrystallization from EtOH-$H_2O$ (1:1); yield 1.68 g (61%) of 26; UV $\lambda$max, pH 1,288 nm ($\epsilon$22,300), pH 11,291 (18,100). Anal. Calcd for $C_{21}H_{26}N_5OPS$ $H_2O$: C, 47.99; H, 5.32; N, 13.32; S, 6.10. Found: C, 47.77; H, 5.48; N, 13.24; S, 6.30.

Method B. In a 2 l, three-neck flask equipped with a thermometer, drying tube, and reflux condensor, a suspension of adenosine cyclic 3', 5'-phosphate (230 g, 0.70 mol) and 1,5-diazabicyclo[5.4.0]undec-5-ene (115 g, 0.75 mol) in 600 ml of dimethylformamide (DMF) was stirred at 60° C. (internal temperature) until a solution was obtained. 2,6-Lutidine (37.4 g, 240 ml) was added dropwise, followed by the slow addition of crotyl bromide (135 g, 1 mol). The reaction mixture was stirred for an additional 5 h at 60° C. The product which had slowly crystallized from solution was filtered, washed with a small volume of DMF and MeOH, and dried to yield 146 g of $N^1$-crotyl-cAMP.

$N^1$-crotyl-cAMP (140 g. 0.365 mol) was dissolved in 800 ml of 1 N NaOH and heated at 75° C. for 2 h. The reaction mixture was cooled and 24 ml of glacial acetic acid added. After the addition of 4.0 g of 5% Pt on carbon, the reaction mixture was shaken under $H_2$ (40 psi for 5 h) until 87 lb of $H_2$ was taken up (91 lb theoretical). The catalyst was filtered and washed with 200 ml of hot $H_2O$. To the combined filtrate plus wash (one l) was added $Br_2$ (61 g, 0.38 mol) in two portions at 30-min intervals. Forty grams of NaOAc was added and the solution was stirred at room temperature. After 4 h, an additional 10 ml of $Br_2$ was added, and stirring was continued for 3 days.

The solution was purged with $N_2$ for 2 h followed by the addition of $NaBH_4$ until the solution gave a negative KI-starch test. The pH was adjusted to 12 with 30% NaOH, and 40 ml of benzyl mercaptan was added. The resulting solution was heated at 70° C. for 1 h and then acidified to pH 1.8 with concentrated HCl. The acidic solution was stirred and allowed to slowly cool. The crude product was filtered and washed with $H_2O$ and then EtOH. The crude material was dissolved in $CHCl_3$ by the addition of triethylamine. The $CHCl_3$ solution was added to a column of 200 g of dry silica gel. The column was washed with $CHCl_3$ and the product eluted with 4% EtOH in $CHCl_3$. The appropriate column fractions were pooled and evaporated. The triethylammonium salt was dissolved in 100 ml of warm 2 N $NH_4OH$, 500 ml of MeOH was added, and the solution was acidified to pH 2 with concentrated HCl. After the solution was cooled, the resulting solid was filtered, washed with $H_2O$ and EtOH, and dried, yielding 101 g of 8-(benzylthio)-6-(n-butylamino)-9-($\beta$-D-ribofuranosyl)- purine cyclic 3', 5'-phosphate which was identical with that prepared by method A.

EXAMPLE 2

Preparation of 8-(benzylthio)-6-piperidino-9-($\beta$-D-ribofuranosyl) purine cyclic 3', 5'-Phosphate A solution of 2'-O-acetyl-8-(benzylthio)-6-chloro-9-($\beta$-D-ribofuranosyl)purine cyclic 3',5'-phosphate sodium salt (1.3 g) in 20 ml of water and 10 ml of piperidine was stirred overnight at room temperature. The solvent was evaporated and the residue triturated twice with ether. The final residue was dissolved in water and placed onto a Dowex 50 ($H^+$,100–200 mesh) 2.5×10 cm column which had been prewashed with methanol-water (1:1). The column was washed with water followed by 100 ml of methanol-water (1:4), 100 ml of methanol-water (1:1), and finally methanol-water (3:1) until all the product was eluted. The fractions containing the product were collected, combined, and evaporated to dryness. The residue was dissolved in boiling ethanol, 5 volumes of water was added, and the solution was ,oncentrated to one-fifth the volume. Upon cooling, 700 mg (59%) of white crystals of 8-(benzylthio)-6-piperidino-9-($\beta$-D-ribofuranosyl)purine cyclic 3',5'-phosphate deposited from the aqueuos solution. Anal. Calcd for $C_{22}H_{26}N_5O_6PS$: C,51.01; H,5.11; N,13.52; S,6.05.

EXAMPLE 3

Preparation of 8-(benzylthio)-6-pyrrolidine-9-($\beta$-D-ribofuranosyl)purine cyclic 3',5'-phosphate A solution of 2'-O-acetyl-8-(benzylthio)-6-chloro-9-($\beta$-D-ribofuranosyl)purine cyclic 3',5'-phosphate (2 g) in 20 ml of $H_2O$ containing 5 ml of pyrrolidine was treated as for the synthesis of the compound of Example 2. Water was added to the residue from the column, and the resulting crystals were filtered and dried to give 947 mg (51%) of 8-(benzylthio)-6-(pyrrolidino)-9-($\beta$-D-ribofuranosyl) purine cyclic 3',5'-phosphate. Anal. Calcd for $C_{21}H_{24}N_5O_6PS.1.5H_2O$: C, 47.36; H, 5.11; N, 13.15. Found: C, 47.05; H, 5.26; N, 12.94.

EXAMPLES 4–7

Using procedures similar to those described in Examples 1–3, the following nucleotides of formula (1) were also prepared, isolated, and purified.

4. 6-(n-butylamino)-8-(methylthio)-9-($\beta$-D-ribofuranosyl)purine cyclic 3',5'-phosphate: UV $\lambda$max pH 1,289 nm ($\epsilon$19,600); pH 11, 290 nm ($\epsilon$17,800), elemental analysis calculated for $C_{15}H_{22}N_5O_6PS$ C, 41.73; H, 5.15; N, 16.24; found C, 41.37; H, 5.23; N, 15.81.

5. 6-(diethylamino)-8-(diethylamino)-9-($\beta$-D-ribofuranosyl)purine cyclic 3',5'-phosphate: UV$\lambda$max pH 1, 289 nm ($\epsilon$18,900); pH 11, 286 nm ($\epsilon$20,000), elemental analysis calculated for $C_{18}H_{29}N_6O_6P$ C, 47.34; H, 6.42; N, 18.42; found C, 47.09; H, 6.30; N, 18.33.

6. 8-(benzylthio)-6-(n-pentylamino)-9-($\beta$-D-ribofuranosyl)purine cyclic 3',5'-phosphate; UV $\lambda$max pH 1, 288 nm ($\epsilon$21,900); pH 11, 291 nm ($\epsilon$17,900) elemental analysis calculated for $C_{22}H_{28}N_5OPS$ C, 50.53; H, 5.42; N, 13.44; found C, 50.89; H, 5.17; N, 13.55.

7. 6-(n-butylmethylamino)-8-(benzylthio)-9-($\beta$-D-ribofuranosyl)purine cyclic 3′,5′-phosphate: UV $\lambda$max pH 1, 288 nm ($\epsilon$21,500); pH 11, 290 nm ($\epsilon$18,700) elemental analysis calculated for $C_{22}H_{28}N_5OPS$ C, 50.53; H, 5.42; N, 13.44; found C, 51.02; H, 5.61; N, 13.63.

The nucleotides of Examples 1 and 3–7 along with various homologs and related prior art nucleotides reported to have antipsoriatic activity were tested for antipsoriatic activity using the animal model and procedures described in the British Journal of Dermatology 94, I, pp. 1–6 (1976). Briefly, this test uses the hairless mouse and its criteria for activity is inhibition of epidermal DNA synthesis (which is indicative of inhibition of proliferation) as evidenced by decrease in incorporation of tritiated thymidine into the DNA of the epidermal cells. In these tests, a 7 cm² area on the mouse's back is exposed to a particular dose of UV irradiation. Such exposure has been shown to cause significant hyperproliferation in the epidermis (as evidenced by increased DNA synthesis) 48 hr after exposure. The test nucleotide is administered to the exposed skin at the desired dose at 1, 18, 24, and 47 hr after UV exposure. The mice are injected with tritiated thymidine at 47 hr and sacrificed at 48 hr. The treated epidermis is removed from the cadaver and lysed. DNA is extracted from the epidermal cell lysate with hydroxylapatite. The incorporation of tritiated thymidine into the DNA is measured by a radiation scintillation counter. Control animals treated only with nucleotide, control animals treated only with vehicle (water-polyvinylalcohol) and control animals exposed to UV irradiation but treated with vehicle lacking the nucleotide are run side-by-side with the UV and nucleotide treated animals for comparison purposes. The nucleotides were applied as a water-poly vinylalcohol formulation (0.000001 to 0.1% by weight nucleotide).

The nucleotide of Example 1 was tested by the above procedure at varying total doses. The drawing shows the results of this testing graphically. The shaded section at the bottom of the graph represents the results for the vehicle treated control animals; the shaded section at the top of the graph represents the results for the UV-treated and vehicle treated controls; the circles represent the results for the UV-treated and nucleotide-treated animals; and the triangles represent the results for the control animals treated only with nucleotide. As shown the nucleotide was effective over a toal dose range of about 0.1 to 15 mcg (normalized for area, about 0.01 to 1.5 mcg/cm²), with maximum effectiveness at about 2–3 mcg total dose (normalized for area, about 0.15–0.25 mcg/cm²). The cyclic nature of the curve shown in the drawing is believed to be attributable to the stimulation of type I protein kinase by the nucleotide at a total dose exceeding about 2–3 mcg. The results reported in the drawing represent data from at least 15 animals at each test dose.

In terms of practical efficacy it is highly desirable, if not essential, that an antiproliferative agent provide therapy to a very high percentage, if not all, of the treated individuals. To that end, the antipsoriatic effectiveness of the compounds in terms of their ability to provide therapy to 100% of the treated animals (at least 5 animals per dose) was determined at each dose as follows.

The rate of DNA synthesis for each group of animals ((no UV (veh.), UV (veh.), UV (drug)) was first expressed as a mean ± standard error. The extent of inhibition of DNA synthesis was calculated by subtracting the mean rate for the non-UV-treated, vehicle treated controls from (1) the UV-treated vehicle treated controls and (2) the UV-treated, drug-treated animals. The difference between the net value for (1) and the net value for (2) was expressed as a % of the net value of (1). The error associated with each % inhibition value was taken as the larger of the standard errors associated with either (1) or (2) (gross values) and converted to a %.

The table below reports the results of these determinations and the standard errors therefrom for the compounds of Examples 1 and 3–7 and related analogs not within the scope of formula (1). (Instances in which the standard error exceeded the determination (ie <100% therapy) are reported as zero.) The columns headed $R_6$ and $R_8$ indicate the substituents at the 6 and 8 positions of the nucleotide. All reported compounds were tested in the free base form.

| | | Inhibition of Epidermal DNA Synthesis (%) Total Dose (ug) | | | | | |
|---|---|---|---|---|---|---|---|
| | | 0.002 | 0.02 | 0.2 | 2 | 20 | 200 |
| | | Concentration Applied (mg/ml) | | | | | |
| $R_6$ | $R_8$ | $10^{-5}$ | $10^{-4}$ | $10^{-3}$ | $10^{-2}$ | $10^{-1}$ | 1 |
| | | Nucleotides of Formula (1) | | | | | |
| —NHnC$_4$H$_9$ | —SCH$_2$C$_6$H$_5$ | 0 | 0 | 0 | 89 ± 27 | 70 ± 32 | 0 |
| —NHnC$_5$H$_{11}$ | —SCH$_2$C$_6$H$_5$ | 0 | 0 | 0 | 0 | 0 | 70 ± 34 |
| —[N(CH$_2$)$_4$] | —SCH$_2$C$_6$H$_5$ | 0 | 0 | 0 | 0 | 0 | 95 ± 18 |
| —N(CH$_3$)nC$_4$H$_9$ | —SCH$_2$C$_6$H$_5$ | 0 | 0 | 0 | 0 | 0 | 35 ± 20 |
| —NHnC$_4$H$_9$ | —SCH$_3$ | 0 | 0 | 0 | 0 | 32 ± 10 | — |
| —N(C$_2$H$_5$)$_2$ | —N(C$_2$H$_5$)$_2$ | 0 | 0 | 0 | 0 | 0 | 60 ± 25 |
| | | Analogs | | | | | |
| —NH$_2$ | —SCH$_2$C$_6$H$_5$ | 0 | 0 | 0 | 0 | 0 | 0 |
| —NHnC$_4$H$_9$ | —H | 0 | 0 | 0 | 0 | 0 | 0 |
| —NHCH$_2$CH$_3$ | —SCH$_2$C$_6$H$_5$ | 0 | 0 | 0 | 0 | 0 | 0 |
| —NHnC$_3$H$_7$ | —SCH$_2$C$_6$H$_5$ | 0 | 0 | 0 | 0 | 0 | 0 |
| —N(nC$_3$H$_7$)$_2$ | —SCH$_2$C$_6$H$_5$ | 0 | 0 | 0 | 0 | 0 | 0 |
| —NHnC$_6$H$_{13}$ | —SCH$_2$C$_6$H$_5$ | 0 | 0 | 0 | 0 | 0 | 0 |

The data of the above table indicate several factors as regards topical antipsoriatic activity of 6,8 substituted ribofuranosylpurine-3′,5′-cylic phosphates. Firstly, the second analog reported ($R_6$=n-butylamino, $R_8$=H) indicates that the substituent at the 8 position of the purine group is essential. This was verified by tests on several other 8-unsubstituted analogs, all of which showed zero antipsoriatic activity. Secondly, the first of the analogs reported ($R_6=NH_2$, $R_8=$benzylthio) indicated that the nitrogen bonded to the 6 position of the purine group must be substituted. The remaining analogs tested indicated that the number of carbon atoms in the 6-position substituent must be 4 or 5. Also, the first analog reported falls within the genus described by U.S. Pat. Nos. 4,007,268 and 4,207,315 and the data show that the compounds of formula (1) have superior topical antipsoriatic activity as compared to that analog.

Modifications of the modes for carrying out the invention described above that are obvious to those of skill in the chemical, biochemical, pharmaceutical, and/or medical arts are intended to be within the scope of the following claims.

We claim:

1. A method of treating a proliferative skin disease comprising topically administering to an afflicted site on the skin of a patient a therapeutically effective amount of a compound of the formula:

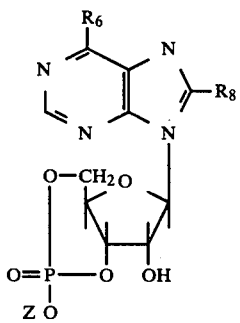

where:
$R_6$ is:
- (i) —$NR_1 R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the —$NR_1 R_2$ group is 4 or 5, or
- (ii) —XR where X is a chalcogen atom of atomic number 8 or 16 and R is alkyl of 4 or 5 carbon atoms, $R_8$ is:
- (i) —X—$(CH_2)_n R_3$ where X is defined previously, n is an integer in the range of 1 to 3, inclusive, $R_3$ is hydrogen, alkyl of 1 to 7 carbon atoms, or phenyl substituted with 0 to 1, inclusive, nitro, halo of atomic number 9 to 35, inclusive, methoxy, hydroxy or methyl, or
- (ii) —$NR_4 R_5$ wherein $R_4$ and $R_5$ are independently selected from the group consisting of hydrogen and alkyl of 1 to 8 carbon atoms and phenalkyl of 7 to 9 carbon atoms, with the provisos that only one of $R_4$ and $R_5$ may be hydrogen and the total number of carbon atoms in the —$NR_4 R_5$ group is in the range of 1 to 9, inclusive, and Z is hydrogen, an alkali metal cation or ammonium.

2. The method of claim 1 wherein $R_6$ is n-butylamino, n-pentylamino, n-butylmethylamino, or pyrrolidyl, $R_8$ is benzylthio, and Z is hydrogen.

3. The method of claim 1 wherein $R_6$ is n-butylamino, $R_8$ is methylthio, and Z is hydrogen.

4. The method of claim 1 wherein $R_6$ is diethylamino, $R_8$ is diethylamino, and Z is hydrogen.

5. The method of claim 1 wherein $R_6$ is n-butylamino, $R_8$ is benzylthio, and Z is hydrogen.

6. The method of claim 1,2,3,4 or 5 wherein the disease is psoriasis.

7. The method of claim 1,2,3,4 or 5 wherein the amount is sufficient to effect preferential and significant activation of type II protein kinase.

8. The method of claim 1,2,3,4 or 5 wherein the amount is in the range of about 0.01 to about 10 mcg/cm² of skin treated.

9. The method of claim 5 wherein the amount is in the range of 0.1 to 1 mcg/cm² of skin treated.

10. The method of claim 1 wherein the compound is administered to the afflicted site via a controlled release dosage form that releases the compound to the skin at a rate that maintains the concentration of the compound in the epidermis at a therapeutically effective level.

11. A topical dosage form for treating a patient for a proliferative skin disease comprising a therapeutically effective amount of at least one compound of the formula:

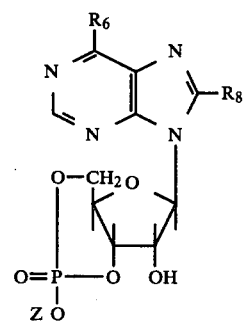

where:
$R_6$ is:
- (i) —$NR_1 R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the —$NR_1 R_2$ group is 4 or 5, or
- (ii) —XR where X is a chalcogen atom of atomic number 8 or 16 and R is alkyl of 4 or 5 carbon atoms, $R_8$ is:
- (i) —R—$(CH_2)_n R_3$ where X is defined previously, n is an integer in the range of 1 to 3, inclusive, $R_3$ is hydrogen, alkyl of 1 to 7 carbon atoms, or phenyl substituted with 0 to 1, inclusive, nitro, halo of atomic number 9 to 35, inclusive, methoxy, hydroxy or methyl, or
- (ii) —$NR_4 R_5$ wherein $R_4$ and $R_5$ are independently selected from the group consisting of hydrogen and alkyl of 1 to 8 carbon atoms and phenalkyl of 7 to 9 carbon atoms, with the provisos that only one of $R_4$ and $R_5$ may be hydrogen and the total number of carbon atoms in the —$NR_4 R_5$ group is in the range of 1 to 9, inclusive, and Z is hydrogen, an alkali metal cation or ammonium admixed with a pharmaceutically acceptable topical carrier.

12. The dosage form of claim 11 wherein $R_6$ is n-butylamino-n-pentylamino, n-butylmethylamino, or pyrrolidyl, $R_8$ is benzylthio, and Z is hydrogen.

13. The dosage form of claim 11 wherein $R_6$ is n-butylamino, $R_8$ is methylthio, and Z is hydrogen.

14. The dosage form of claim 11 wherein $R_6$ is diethylamino, $R_8$ is diethylamino, and Z is hydrogen.

15. The dosage of claim 11, wherein $R_6$ is n-butylamino, $R_8$ is benzylthio, and Z is hydrogen.

* * * * *

REEXAMINATION CERTIFICATE (370th)
United States Patent [19]
Miller et al.

[11] B1 4,369,181
[45] Certificate Issued   Jul. 16, 1985

[54] PROCESS FOR TREATING PROLIFERATIVE SKIN DISEASES USING CERTAIN 6,8-SUBSTITUTED RIBOFURANOSYLPURINE-3',5'-CYCLIC PHOSPHATES

[75] Inventors: Jon P. Miller, Foster City; Wesley W. Zmolek, Fremont, both of Calif.

[73] Assignee: SRI International, Menlo Park, Calif.

Reexamination Request:
No. 90/000,594, Jul. 13, 1984

Reexamination Certificate for:
Patent No.: 4,369,181
Issued: Jan. 18, 1983
Appl. No.: 290,223
Filed: Aug. 5, 1981

[51] Int. Cl.³ .................. A61K 31/70; C07H 19/20
[52] U.S. Cl. ........................... 514/47; 514/48; 536/27; 536/28
[58] Field of Search .............. 424/180; 536/26, 27, 536/28, 29

[56] References Cited
U.S. PATENT DOCUMENTS

| | | | |
|---|---|---|---|
| 4,007,268 | 2/1977 | Voorhees | 424/200 |
| 4,207,315 | 6/1980 | Voorhees et al. | 424/200 |

FOREIGN PATENT DOCUMENTS

| | | | |
|---|---|---|---|
| 1426479 | 6/1973 | United Kingdom | 424/180 |

*Primary Examiner*—Johnnie R. Brown

[57] ABSTRACT

Proliferative skin diseases such as psoriasis are treated by topically administering cAMP analogs of the following formula to the afflicted skin site at a dose that preferentially and significantly activates type II protein kinase:

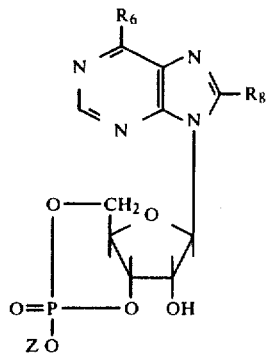

where:

$R_6$ is:
(i) $-NR_1 R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the $-NR_1 R_2$ group is 4 or 5, or
(ii) $-XR$ where X is a chalcogen atom of atomic number 8 or 16 and R is alkyl of 4 or 5 carbon atoms, $R_8$ is:
(i) $-X-(CH_2)_n R_3$ where X is defined previously, n is an integer in the range of 1 to 3, inclusive, $R_3$ is hydrogen, alkyl of 1 to 7 carbon atoms, or phenyl substituted with 0 to 1, inclusive, nitro, halo of atomic number 9 to 35, inclusive, methoxy, hydroxy or methyl, or
(ii) $-NR_4 R_5$ wherein $R_4$ and $R_5$ are independently selected from the group consisting of hydrogen, alkyl of 1 to 8 carbon atoms, and phenalkyl of 7 to 9 carbon atoms with the provisos that only one of $R_4$ and $R_5$ may be hydrogen and the total number of carbon atoms in the $-NR_4 R_5$ group is in the range of 1 to 9, inclusive, and Z is hydrogen, an alkali metal cation or ammonium.

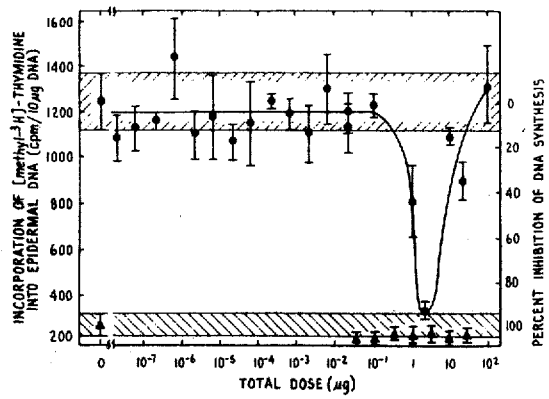

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

The patentability of claims 3, 4, 13 & 14 is confirmed.

Claims 1, 6–8 and 11 are determined to be patentable as amended.

Claims 2, 5, 9, 10, 12 and 15, dependent on an amended claim, are determined to be patentable.

1. A method of treating a proliferative skin disease comprising topically administering to an afflicted site on the skin of a patient a therapeutically effective amount of a compound of the formula:

[
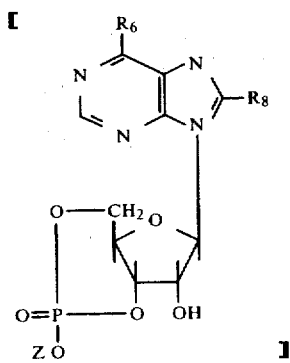
]

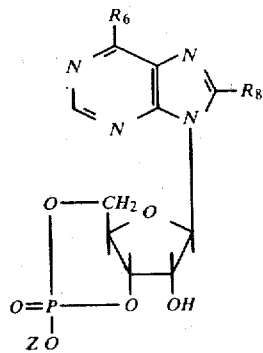

where:
$R_6$ is:
  (i) —$NR_1R_2$ where $R_1$ and $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the —$NR_1R_2$ group is 4 to 5, or
  (ii) —XR where X is a chalcogen atom of atomic number 8 or 16 and R is alkyl of 4 or 5 carbon atoms,
$R_8$ is:
  [(i)] —X—$(CH_2)_nR_3$ where X is defined previously, n is an integer in the range of 1 to 3, inclusive, $R_3$ is [hydrogen, alkyl of 1 to 7 carbon atoms, or] phenyl substituted with 0 to 1, inclusive, nitro, halo of atomic number 9 to 35, inclusive, methoxy, hydroxy or methyl, [or
  (ii) —$NR_4R_5$ wherein $R_4$ and $R_5$ are independently selected from the group consisting of hydrogen and alkyl of 1 to 8 carbon atoms and phenalkyl of 7 to 9 carbon atoms, with the provisos that only one of $R_4$ and $R_5$ may be hydrogen and the total number of carbon atoms in the —$NR_4R_5$ group is in the range of 1 to 9, inclusive,] and Z is hydrogen, an alkali metal cation or ammonium.

6. The method of claim 1, 2, [3, 4] or 5 wherein the disease is psoriasis.

7. The method of claim 1, 2, [3, 4] or 5 wherein the amount is sufficient to effect preferential and significant activation of type II protein kinase.

8. The method of claim 1, 2, [3, 4] or 5 wherein the amount is in the range of about 0.01 to about 10 mcg/cm² of skin treated.

11. A topical dosage form for treating a patient for a proliferative skin disease comprising a therapeutically effective amount of at least one compound of the formula:

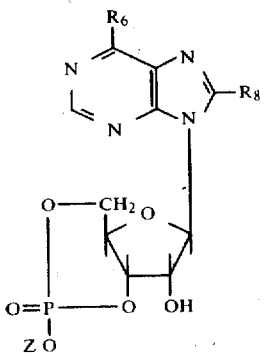

where:
$R_6$ is:
  (i) —$NR_1R_2$ where $R_1$ $R_2$ are independently selected from the group consisting of hydrogen, alkyl of 1 to 5 carbon atoms, and cyclopentyl or are joined together with the nitrogen atom to form a hetrocyclic group having 4 to 5, inclusive, annular carbon atoms with the proviso that the total number of carbon atoms in the —$NR_2R_2$ group is 4 or 5, or
  (ii) —XR where X is a chalcogen atom of atomic number of 8 or 16 and R is alkyl of 4 or 5 carbon atoms,
$R_8$ is:
  [(i) —R—$(CH_2)_nR_3$] —X—$(CH_2)_nR_3$ where X is defined previously, n is an integer in the range of 1 to 3, inclusive, $R_3$ is [hydrogen, alkyl of 1 to 7 carbon atoms, or] phenyl substituted with 0 to 1, inclusive, nitro, halo of atomic number 9 to 35, inclusive, methoxy, hydroxy or methyl, [or
  (ii) —$NR_4R_5$ wherein $R_4$ and $R_5$ are independently selected from the group consisting of hydrogen and alkyl of 1 to 8 carbon atoms and phenalkyl of 7 to 9 carbon atoms, with the provisos that only one of $R_4$ and $R_5$ may be hydrogen and the total number of carbon atoms in the —$NR_4R_5$ group is in the range of 1 to 9, inclusive,] and Z is hydrogen, an alkali metal cation or ammonium admixed with a pharmaceutically acceptable topical carrier.

* * * * *